United States Patent
Demco

[11] Patent Number: 5,743,881
[45] Date of Patent: Apr. 28, 1998

[54] LAPAROSCOPIC SURGICAL INSTRUMENT AND METHOD OF USING SAME

[75] Inventor: Lawrence A. Demco, Calgary, Canada

[73] Assignee: Aptec Medical Corporation, Calgary, Canada

[21] Appl. No.: 552,863

[22] Filed: Nov. 3, 1995

[51] Int. Cl.$^6$ .................................................. A61M 5/00
[52] U.S. Cl. .................................................. 604/164; 604/158
[58] Field of Search .................................. 604/164, 165, 604/166, 167, 168, 169, 158

[56] References Cited

U.S. PATENT DOCUMENTS

| | | | |
|---|---|---|---|
| 3,459,183 | 8/1969 | Ring et al. | 604/165 |
| 4,763,667 | 8/1988 | Manzo. | |
| 4,869,717 | 9/1989 | Adair. | |
| 4,978,334 | 12/1990 | Toye. | |
| 5,106,376 | 4/1992 | Monomen et al.. | |
| 5,139,487 | 8/1992 | Baber | 604/164 |
| 5,158,543 | 10/1992 | Lazarus | 604/164 |
| 5,258,003 | 11/1993 | Ciaglia. | |
| 5,334,150 | 8/1994 | Kaali. | |
| 5,336,176 | 8/1994 | Yoon. | |
| 5,368,574 | 11/1994 | Antonacci et al.. | |

FOREIGN PATENT DOCUMENTS 2 182 666  12/1973  France.

OTHER PUBLICATIONS

Endopath Brochure ©1994.
Versaport Brochure ©1994.
"An Alternative Technique to Create the Pneumoperitoneum for Laparoscopic Surgery" Surgical Laparoscopy & Endoscopy, vol. 5, No. 3, 1995 H.M. Lazarus.

*Primary Examiner*—Sam Rimell
*Assistant Examiner*—Luke J. Yeh
*Attorney, Agent, or Firm*—Bennett Jones Verchere

[57] ABSTRACT

A surgical trocar instrument is taught which is useful for conducting laparoscopic procedures using local anesthetic. The instrument is used to anesthetize a path through the abdominal wall and to guide the instrument along the anesthetized path. The instrument includes a trocar and cannula which are mounted on and are guided by a hypodermic needle.

16 Claims, 4 Drawing Sheets

LAPAROSCOPIC SURGICAL INSTRUMENT AND METHOD OF USING SAME

FIELD OF THE INVENTION

This invention relates to the field of laparoscopic access and, in particular, to laparoscopic surgical instruments and methods for using such instruments.

BACKGROUND OF THE INVENTION

Laparoscopic based diagnostic and operative procedures are conducted using laparoscopic surgical instruments which act as ports through the abdominal wall and into the peritoneal cavity. Such instruments are formed of a central trocar which is elongate and which has a sharpened, tipped end suitable for insertion through layers of the abdominal wall and the peritoneum surrounding the peritoneal cavity. The trocar is surrounded by a hollow trocar sleeve or cannula which is removable from the trocar.

Conventional laparoscopic procedures involve the insertion of the trocar and cannula assembly through the abdominal wall and into the peritoneal cavity while the patient is under general anesthetic. After insertion, the trocar is withdrawn from the cannula, leaving the cannula inserted to provide a port to the interior of the cavity. Various surgical procedures are carried out through the cannula by the use of remotely operable instruments, such as laparoscopes and biopsy instruments, in a conventional known manner.

Because of increasing medical and hospitalization costs, it is desirable to perform laparoscopic procedures on an outpatient basis. For such procedures, local anesthesia is preferred over general anesthesia because of its decreased risk and accelerated recovery rate for patients. Current laparoscopic procedures which use local anesthetic require random administration of anesthetic by syringe at the planned point of insertion of the trocar. Random administration of anesthetic by syringe is often inaccurate and results in incomplete anesthesia of the path of penetration through the abdominal wall. This causes increased patient discomfort and increases the requirement for a general anesthetic to complete the procedure.

SUMMARY OF THE INVENTION

A laparoscopic instrument has been invented which can be introduced under local anesthetic. To afford the use of local anesthetic, the instrument includes a needle through which the anesthetic can be administered. The needle is used to anesthetize a path for insertion of the instrument and to guide the instrument along the anesthetized path. The instrument of the present invention enhances the outpatient capabilities of laparoscopic procedures and allows for use of the procedure with greater patient comfort over other laparoscopic procedures using randomly applied local anesthetic.

According to a broad aspect of the present invention there is provided a laparoscopic instrument comprising a tubular member having an end formed for insertion through a body wall and a tubular sleeve disposed thereabout, the tubular member defining a lumen for accepting a needle for administration of fluids.

According to a still further broad aspect of the present invention there is provided a laparoscopic instrument comprising: a needle suitable for the administration of fluids having a sharpened tip and a bore therethrough; a member having an end formed for insertion through tissue and having a lumen therein for accepting the needle, the lumen being disposed to allow extension of the sharpened tip of the needle from the end formed for insertion through tissue, the needle being slidable within the lumen; and, a sleeve disposed about the member.

According to another broad aspect of the present invention there is provided a method of inserting a surgical device through tissue comprising the steps of: (a) providing a surgical device having a needle suitable for administration of fluids and a member disposed about the needle and slidable therealong, the member having an end formed for insertion through tissue; (b) penetrating the tissue with the needle and administering an amount of anesthetic to the tissue through the needle; and, (c) moving the member along the needle such that the tissue is penetrated with the end formed for insertion through tissue.

DESCRIPTION OF THE INVENTION

The laparoscopic instrument of the present invention is comprised of a trocar and cannula assembly having a needle for administration of fluids disposed within a lumen formed in the trocar. The needle provides for the administration of a local anesthetic to a selected region of tissue to anesthetize that tissue and the needle is further used as a guide to direct the penetration of the trocar directly through the anesthetized tissue. In one embodiment, the needle is also used to confirm the placement of the needle tip within the peritoneal cavity. After penetration of the peritoneal cavity, the needle can be used for administration of other fluids such as, for example, saline and carbon dioxide for irrigation or insufflation.

While the cannula of the present laparoscopic instrument is generally as known in the art of laparoscopic surgery, the trocar of the present invention has formed therein a lumen to accommodate the needle. The lumen opens at the sharpened tip of the distal end of the trocar so that when the needle is placed in the lumen of the trocar, the needle tip can be extended from the sharpened tip of the trocar.

The needle is formed to be slidably mounted in the lumen of the trocar. The needle is selected for administration of fluids such as anesthetic and has a suitable gauge to allow such administration. Further, the needle is formed to be sufficiently strong to allow the trocar/cannula assembly to ride therealong. The needle is disposed in the trocar in any suitable way so that the instrument is adjustable between a first configuration position in which the needle is extended beyond the tip of the trocar for administration of fluids and a second configuration in which the trocar can be moved along and guided by the needle.

In one embodiment an elongate needle is used in combination with a trocar having a lumen of uniform diameter extending from its proximal end to its distal end. The instrument is moved between the first and second configurations by manually moving the trocar/cannula assembly and needle relative to one another. In use, a syringe containing anesthetic is attached to the needle. Anesthetic is fed from the syringe directly into the bore of the needle for administration.

In another embodiment, a needle is mounted in the tip of the trocar and is controlled by a mechanism which is adjustable between a configuration in which the needle is maintained in an extended position for administration of anesthetic and a configuration which allows the trocar/cannula to ride over the needle for penetration of the abdominal wall by the trocar/cannula assembly. The needle bore is in communication with the lumen of the trocar to accept fluids passed therethrough. The trocar at the proximal opening of the lumen is fitted with a suitable connector, such as a luer lock, to accept a syringe or tube. Anesthetic is fed through the lumen of the trocar to the needle for administration.

In still another embodiment, a needle member is used which is comprised of a needle bonded to an elongate, tubular member. The needle and attached tubular member are inserted through the lumen of the trocar such that the lumen of the trocar accommodates the tubular member while the needle extends from the lumen at the sharpened tip of the trocar. The instrument is adjusted between the first and second configurations by manually moving the trocar/cannula assembly and the tubular member relative to one another. The proximal end of the tubular member is preferably formed to define a connection for medical equipment such as a syringe. Anesthetic is fed from an attached syringe to the bore of the tubular member and into the bore of the needle for administration.

In use, the instrument is assembled such that the needle is disposed in the lumen of the trocar, with the sharpened tip of the needle being extendable from the sharpened tip of the trocar. The trocar is inserted in the cannula. A syringe containing a suitable anesthetic is attached to the appropriate coupler which is in communication with the bore of the needle.

The needle of the assembled instrument is then used to administer anesthetic to the patient at the anticipated point of insertion of the instrument. While the needle remains inserted to the patient, the trocar/cannula assembly is urged along the length of the needle to penetrate the patient's tissue directly at the point of administration of the anesthetic. The assembly is urged along the needle a suitable distance until it is almost adjacent the extent of penetration of the needle. The introduction of the trocar/cannula assembly through the abdominal wall can be accomplished in steps by first advancing the needle a short distance followed, after the administration of anesthetic, by the advancement of the trocar/cannula assembly. In a preferred embodiment, the needle is used to administer anesthetic to the abdominal wall to form an anesthetized path directly into the body cavity prior to penetration of the body wall by the trocar. This allows the trocar to be inserted through the body wall and into the body cavity in one smooth, continuous operation. Preferably, a small incision is made through the skin layers at the point of insertion of the needle to avoid forceful entry of the trocar/cannula assembly through intact skin. Preferably also, confirmation of placement of the needle tip within the body cavity is carried out by any suitable means prior to introduction of the trocar/cannula assembly. Suitable confirmation means include, for example, the use of a wire for insertion through the needle bore or the injection of additional anesthetic or saline through the needle and aspiration back into the syringe to determine the presence of blood.

When access is gained to the peritoneal cavity, the syringe containing anesthetic can be removed and the hypodermic needle can be used to administer sterile saline for aspiration or gas for inflation of the cavity. Alternatively, the syringe, the needle, and, if desired, the trocar can be removed leaving the cannula in place to define an access port into the peritoneal cavity through which the laparoscopic procedure can proceed.

BRIEF DESCRIPTION OF THE DRAWINGS

A further, detailed, description of the invention, briefly described above, will follow by reference to the following drawings of specific embodiments of the invention. These drawings depict only typical embodiments of the invention and are therefore not to be considered limiting of its scope. In the drawings.

DETAILED DESCRIPTION OF THE PREFERRED EMBODIMENTS

While a cannula and a trocar for use in the laparoscopic instrument of the present invention are described and illustrated herein, it is to be understood that the cannula and/or the trocar can be modified for other similar surgical procedures and can be of any suitable type, for example having gas delivery ports, or formed of any suitable material, provided that the needle can be accommodated by the trocar and the trocar can be moved along the needle.

Figure 1:
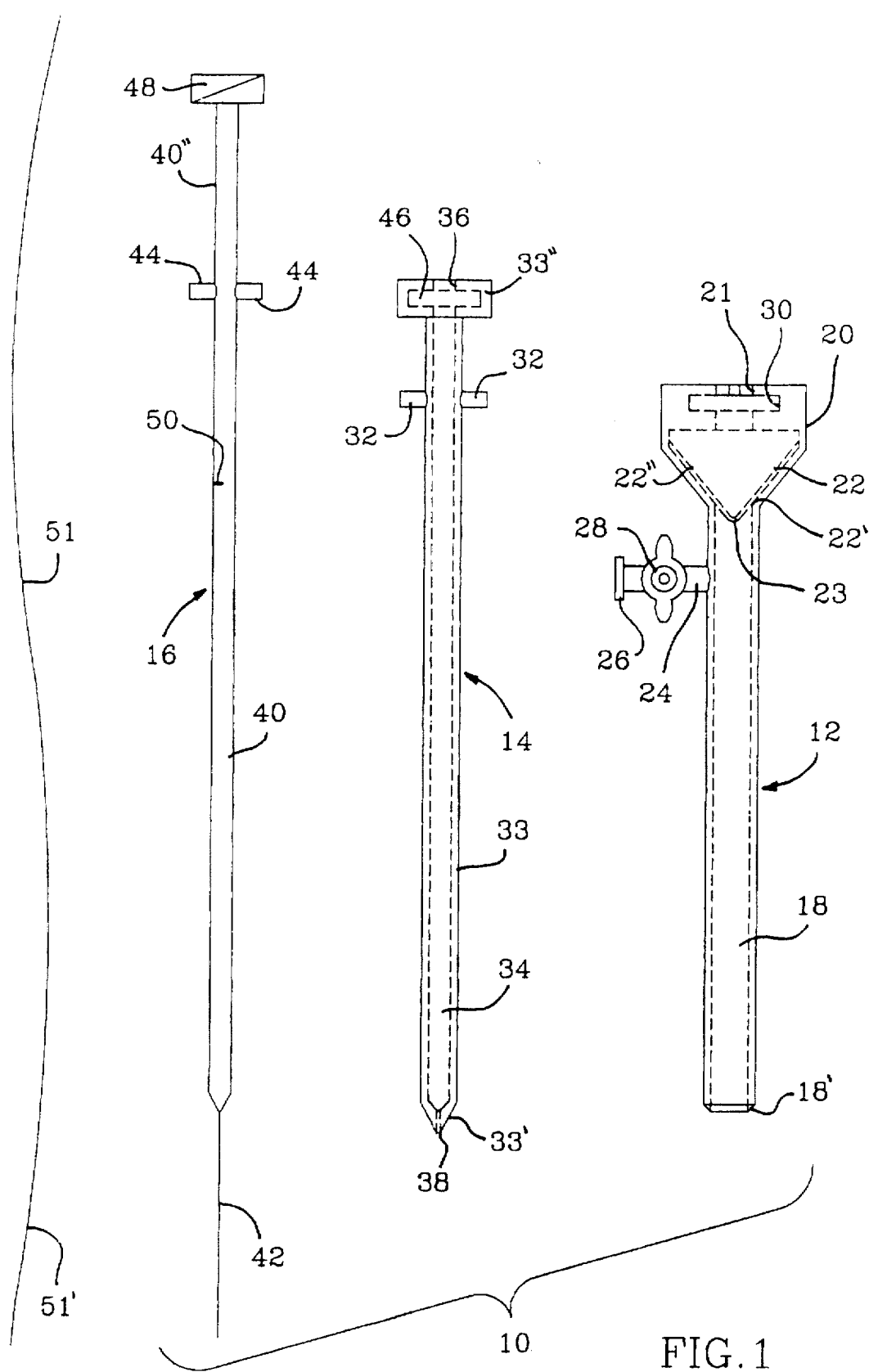
FIG. 1 is a view of the unassembled components of the laparoscopic instrument of the present invention.
Figures 2A, 2B:
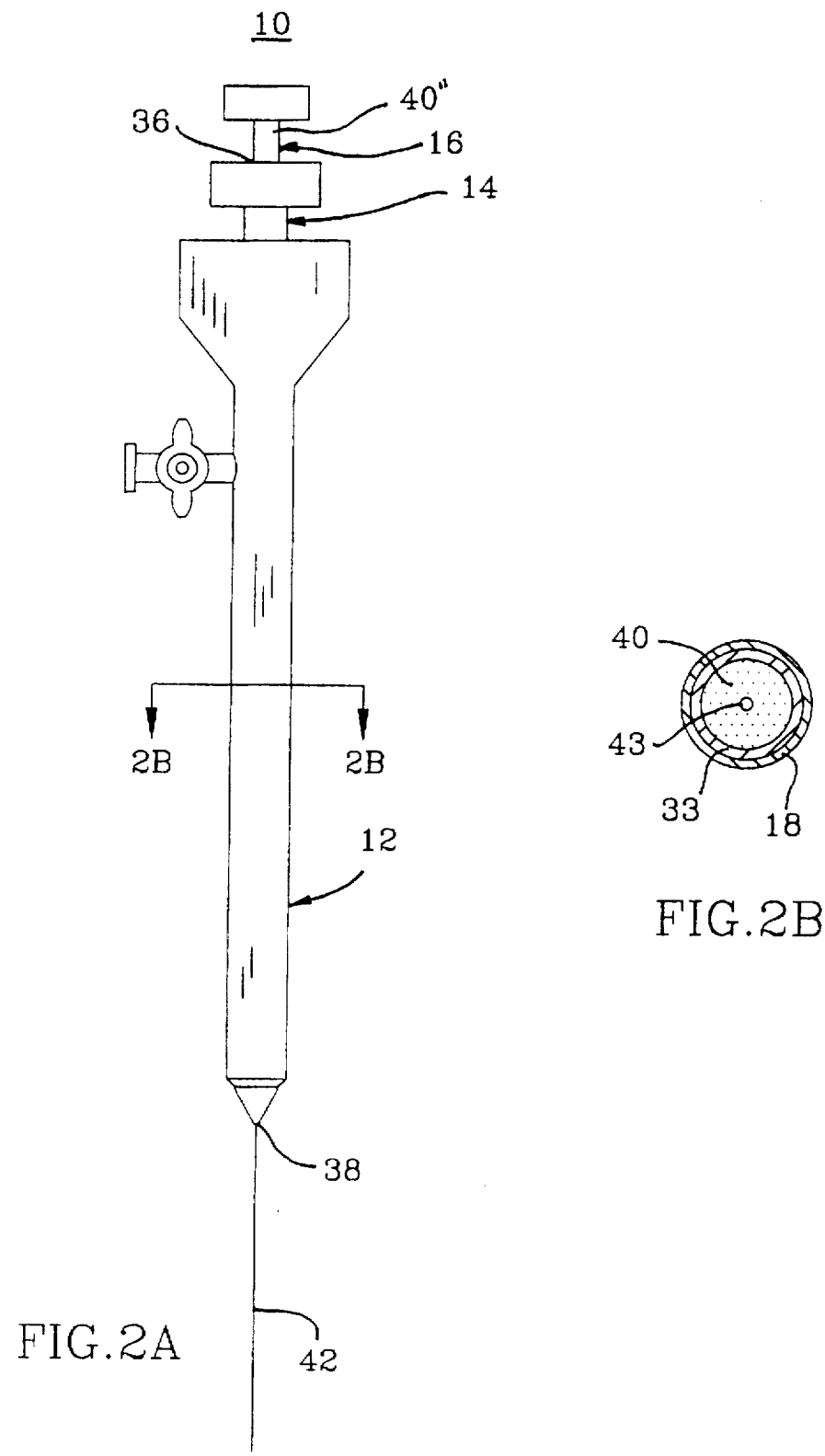
FIG. 2A is a sectional longitudinal view of the assembled laparoscopic instrument of the present invention.
FIG. 2B is a cross sectional view of the assembled laparoscopic instrument of FIG. 2A at the location shown by the indicia 2B—2B.

Referring to FIG. 1, a laparoscopic instrument 10 of the present invention is shown disassembled. Reference is also made to FIGS. 2A and 2B, wherein instrument 10 is shown assembled for use. Instrument 10 includes a cannula 12, a trocar 14, and a needle member 16.

Cannula 12 includes a sleeve 18 and a proximal, handling portion 20. Sleeve 18 is formed of material suitable for use in surgical instruments such as, for example, stainless steel or medical grade plastic. Distal tip 18' of sleeve 18 is bevelled to facilitate its passage through tissue. Sleeve 18 is thin-walled so as to minimize the outer diameter of the instrument and is of a suitable length to extend through the abdominal wall which will depend on the abdominal wall thickness in each patient. For example, a suitable cannula for use in a diagnostic laparoscopic procedure (using a mini-laparoscope) for an adult patient of average size can be 18 to 25 cm in length and 5 to 6 mm in diameter.

Handling portion 20 is formed to be suitable for grasping by a person using the instrument and is formed integral with sleeve 18. Alternatively, handling portion 20 is formed separately and is bonded to sleeve 18. Handling portion 20 has an opening 21 for communication with the bore of sleeve 18 and houses a diaphragm valve 22, shown in phantom. Valve 22 comprises membranes 22' and 22" which abut to form a slit 23 for allowing passage of instruments (not shown) therethrough while conforming to the shape of the instrument to seal against the escape of gases or liquids. Preferably, membranes 22', 22" are formed of material such as silicone rubber.

Cannula 12 further includes a port 24 which opens into sleeve 18 for introduction of fluids to the inner bore of sleeve 18. Port 24 includes a luer lock fitting 26 for releasably locking an instrument in place and a stop cock 28 for controlling the passage of fluids through the port.

Cannula 12 accepts and closely surrounds trocar 14. In use, trocar 14 is slidably disposed within cannula 12 and extends beyond each end of the cannula. To facilitate the sliding of trocar 14 within cannula 12, the outer surface of the trocar can be lubricated with a suitable inert lubricant such as, for example, silicone. Preferably, trocar 14 is locked within cannula 12 to be slidable within the cannula only when the lock is released. For that purpose female lock channels 30 are provided on cannula 12 which accept lock pins 32 on trocar 14. Lock channels 30 and pins 32 together form a quarter-turn, pin-in-channel lock assembly. Each channel 30 is "L"-shaped and formed to accept a pin 32 through an opening. The openings are spaced on the cannula to allow the pins to simultaneously enter the channels. Once inserted, the pins are moved further into the channels by twisting the trocar a quarter turn relative to the cannula. The channels are tapered slightly at their inner ends to frictionally engage the lock pins. The lock pins are removed from the channels by twisting the trocar, relative to the cannula, a quarter turn in the opposite direction.

Trocar 14 is an elongate member having a body 33 with a sharpened distal tip 33' formed for insertion through tissue. Tip 33' is conical or pyramidal in shape and is sufficiently sharp to be able to be penetrate and be physically pressed through the layers of skin, connective tissue and the peritoneum in the abdominal wall of a patient, in order to gain access to the interior of the peritoneal cavity. Proximal end 33" of trocar 14 supports lock pins 32 and is enlarged to form a handle. Proximal end 33" can be formed integral with body 33 or can be formed separately and bonded thereto. Trocar 14 is formed from any suitable material useful for production of surgical instruments such as, for example, stainless steel or medical grade plastic.

Trocar 14 has formed therein a lumen 34, shown in phantom. Openings 36 and 38 at proximal end 33" and distal tip 33', respectively, allow access to lumen 34. Lumen 34 is formed to accept and closely surround needle member 16. Lumen 34 adjacent distal tip 33' is narrowed to prevent needle member from passing fully through lumen 34 and to support member 16.

In the preferred embodiment, member 16 includes a tube 40 having a needle 42 bonded thereto. The inner bore 43 of tube 40 is in communication with the inner bore (not shown) of needle 42. Tube 40 is preferably formed of injection moulded, clear plastic. Lock pins 44 are provided on tube 40 for cooperation with female lock channels 46 formed in proximal end 33" of trocar 14. Lock assembly 44, 46 allows the locking of member 16 into engagement with trocar 14 for purposes of transport or use where member 16 must be supported within lumen 34. A luer lock connection 48 is formed at proximal end 40" of tube 40 for connection to medical instruments such as syringes and intravenous tubing.

In use, elongate member 16 is slidably disposed in lumen 34 and can extend out through openings 36 and 38. The outer surface of tube 40 may be lubricated with a suitable inert lubricant such as, for example, silicone to facilitate the sliding movement of member 16 within trocar 12.

Needle 42 is bonded to tube 40 in a suitable way which will allow communication between the inner bore of tube 40 and the bore of needle 42. Needles of various gauges and lengths are useful depending on the patient requirements.

To identify the positioning of member 16 within lumen 34 of trocar 14, a marker 50 is provided on tube 40. Marker 50 is positioned along tube 40 to indicate that the tip of needle 42 is adjacent to tip 33' of trocar 14.

For use in confirmation of placement of needle 42 within a body cavity, preferably, a wire 51 having a flexible tip 51' is provided for use with the instrument. A distance marker is marked on wire 50 to indicate, during use, that tip 51' is even with the tip of the needle. Wire 51 and is preferably formed entirely of stainless steel and has a suitable diameter to permit its easy passage through the bore of needle 42. The end of flexible tip 51' is formed blunt to avoid injuring the patient during use.

Laparoscopic instrument 10 of the present invention is assembled in preparation for use, by placing trocar 14 in the bore of cannula 12 such that sharpened tip 33' is exposed at tip 18' of cannula 12. Member 16 is, in turn, placed in lumen 34 of trocar 14 such that hypodermic needle 42 extends through opening 38 and proximal end 40" of tube 40 extends through opening 36.

Figure 3A:
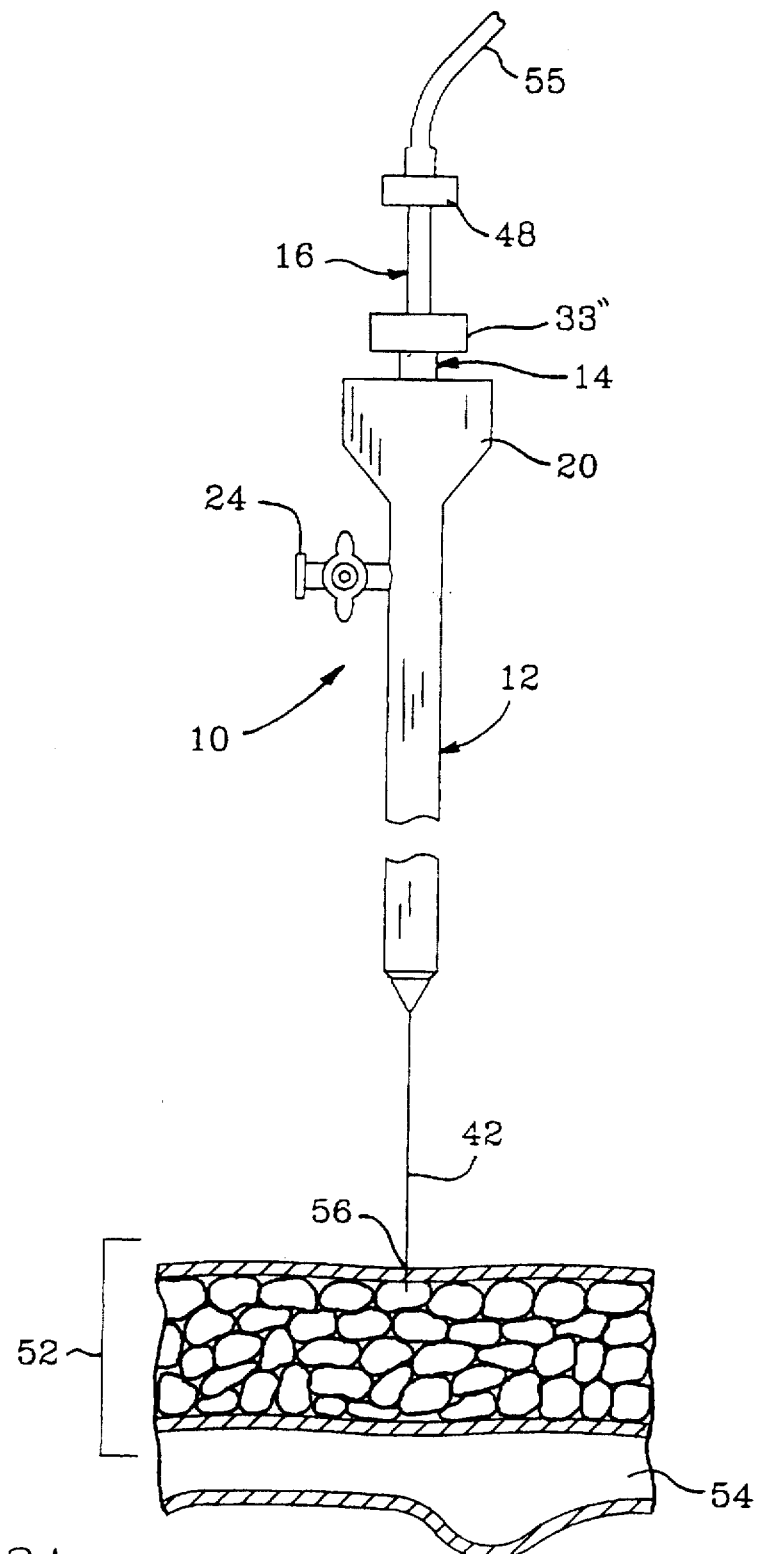
FIGS. 3A, 3B and 3C are broken side sequential views of a distal end of a laparoscopic instrument according to the present invention in an operative state during penetration of an abdominal wall.

The instrument of the present invention is used to penetrate a patient's abdominal wall to gain access to the peritoneal cavity. Referring to FIG. 3A, in the first step of an exemplary penetration procedure, instrument 10, as shown in FIG. 2A, is removed from its sterile packaging and a tube 55 for conducting anesthetic is attached at luer lock connection 48 of member 16. After suitable patient prepping, instrument 10 is grasped at 20 and 33" and needle 42 is inserted at the planned point of insertion 56 on the patients abdomen and an amount of anesthetic is administered to affect anesthesia at the insertion point.

The needle is then removed from the patient and a small skin incision 57 (FIG. 3B) is made at the anesthetized point by use of a scalpel.

Figure 3B:
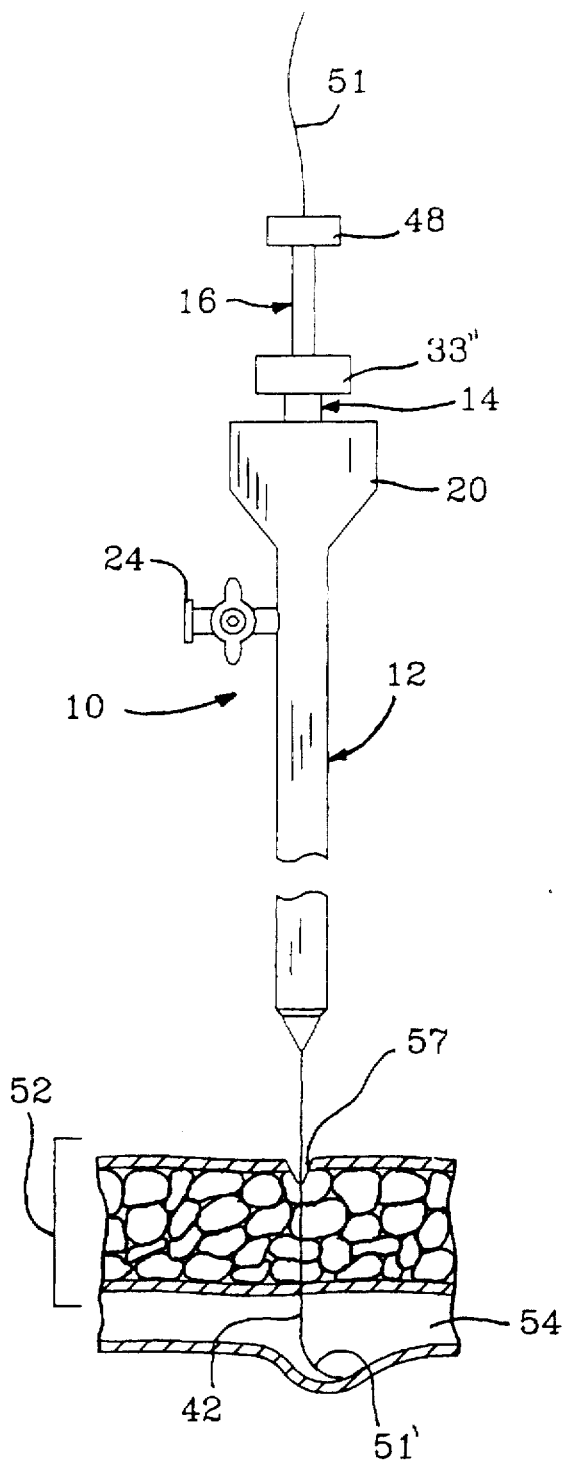

Referring to FIG. 3B, needle 42 is inserted into incision 57 and a further amount of anesthetic is administered to the tissue. Needle 42 is advanced in a series of steps, which include advancement of the needle and the administration of anesthetic to form an anesthetized path. This is repeated until the needle tip passes into the peritoneal cavity 54. Placement of the needle within peritoneal cavity 54 is confirmed by insertion of wire 51. In this method, tube 55 is removed from member 16 and wire 51 is inserted through member 16 and into the bore of needle 42. When flexible tip 51' of wire 51 can be inserted beyond the tip of needle 42, as determined by monitoring the length of wire inserted, placement of the needle tip within the cavity is confirmed.

The wire can then be removed from the member and a gas supply can be connected to the member 16 for insufflation of the cavity.

Figure 3C:
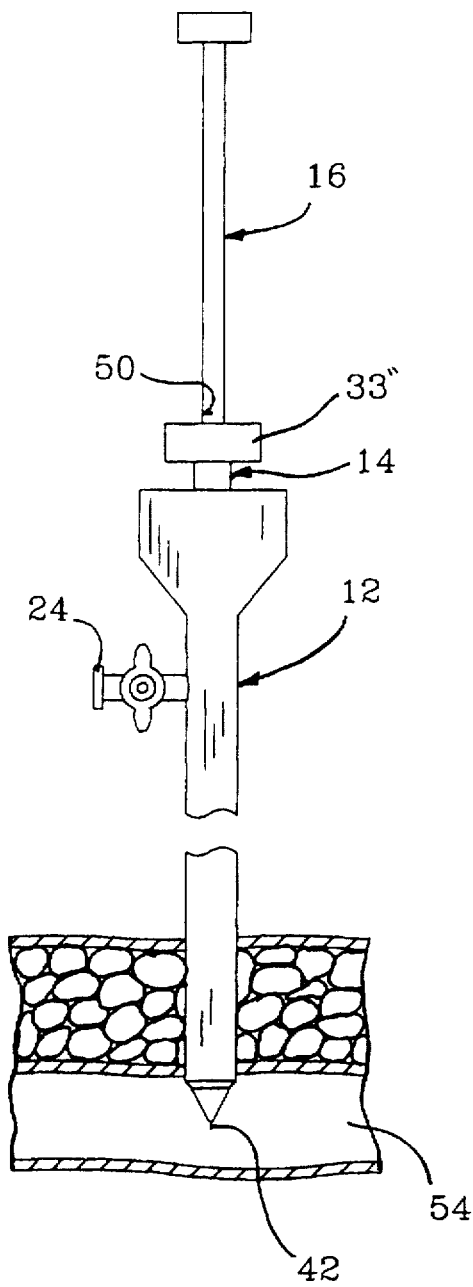

Referring to FIG. 3C, while needle 42 remains in place, trocar 14 and cannula 12, which are locked together, are slowly advanced along member 16 to penetrate the patient's abdomen. The trocar is advanced until marker 50 is visible above proximal end 33" of trocar 14 which indicates that tip 33' of trocar 14 has reached the tip of the needle and is also in peritoneal cavity 54.

The instrument can then be handled as desired. For example, member 16 and trocar 14 can remain in place to inject sterile saline or carbon dioxide by replacement of tubing 55 with other suitable apparatus. Alternatively or afterward, member 16 and trocar 14 can be drawn out of cannula 12, by releasing lock pins 32 from female lock portion 30. When member 16 and trocar 14 are removed, cannula 12 remains in place in the wall. Gas or liquid are retained in peritoneal cavity 54 by the diaphragm valve in cannula 12. The laparoscopic procedure can then proceed by insertion of surgical instruments through cannula 12 and addition of gas or liquids through port 24.

It will be apparent that many changes may be made to the illustrative embodiments, while falling within the scope of the invention and it is intended that all such changes be covered by the claims appended hereto.

The embodiments of the invention in which an exclusive property or privilege is claimed are defined as follows:

1. A surgical instrument comprising:
    a needle suitable for the administration of fluids having a sharpened tip and a bore therethrough;

a member having an end formed as a sharpened tip for insertion through tissue and having a lumen therein for accepting the needle, the lumen being disposed to allow extension of the sharpened tip of the needle from the end formed for insertion through tissue, the needle being slidable within the lumen and the lumen being formed to permit the member to ride along the needle;

a sleeve disposed about the member; and, a wire sized to pass through the bore of the needle.

2. The surgical instrument as claimed in claim 1 wherein the lumen extends along the member's length to open at each end of the member and the needle is formed to extend the full length of the lumen.

3. The surgical instrument as claimed in claim 2 wherein the needle has bonded thereto a tubular member having a bore therethrough in fluid connection with the bore of the needle.

4. The surgical instrument of claim 3 wherein the lumen has an inner diameter and the inner diameter is reduced adjacent the end formed for insertion through tissue.

5. The surgical instrument of claim 3 wherein a releasable lock is disposed between the member and the sleeve.

6. The surgical instrument of claim 2 wherein the lumen is formed to closely surround the needle.

7. The surgical instrument of claim 1 wherein the lumen is formed to closely surround the needle.

8. The surgical instrument of claim 1 wherein a releasable lock is disposed between the member and the sleeve.

9. A method for inserting a surgical device through tissue comprising the steps of:

(a) providing a surgical device having a needle suitable for the administration of fluids having a sharpened tip and a bore therethrough; a member having an end formed as a sharpened tip for insertion through tissue and having a lumen therein for accepting the needle, the lumen being disposed to allow extension of the sharpened tip of the needle from the end formed for insertion through tissue, the needle being slidable within the lumen and the lumen being formed to permit the member to ride along the needle; and a sleeve disposed about the member;

(b) penetrating the tissue with the needle and administering an amount of anesthetic to the tissue through the needle;

(c) moving the member and the sleeve along the needle such that the tissue is penetrated with the end formed for insertion through tissue.

10. The method of claim 9 used to gain access to a body cavity and wherein the tissue is penetrated with the needle and anesthetic is administered to the tissue until access is made to the body cavity prior to moving the member along the needle.

11. The method of claim 10 wherein after access is gained to a body cavity the needle and member are removed from the sleeve.

12. The method of claim 10 further comprising the step of: inserting a wire through the bore of the needle to determine when the needle has gained access to the body cavity.

13. The method of claim 9 used to gain access to a body cavity.

14. The method of claim 9 further comprising:

(d) repeating steps (b) and (c) until access is gained to a body cavity; and (e) removing the needle and the member from the sleeve.

15. The method of claim 9 wherein the sleeve is sized to permit a laparoscopic procedure to be performed therethrough.

16. The method of claim 9 further comprising the step of: inserting a wire through the bore of the needle to determine the positioning of the needle in the tissue.

* * * * *